US012766084B2

(12) United States Patent
Kim et al.

(10) Patent No.: US 12,766,084 B2
(45) Date of Patent: Oct. 20, 2026

(54) COMPOSITION COMPRISING REGENTIDE-034 AND REGENTIDE-041 FOR SKIN CARE OR WRINKLE REDUCTION

(71) Applicant: NINEBIOPHARM CO., LTD., Cheongju-si (KR)

(72) Inventors: Jae Hwan Kim, Sejong-si (KR); Ji Heon Rhim, Sejong-si (KR); Ri Ra Lee, Gwangju-si (KR); Hye In Ahn, Osong-eup (KR)

(73) Assignee: NINEBIOPHARM CO., LTD., Cheongju-si (KR)

(*) Notice: Subject to any disclaimer, the term of this patent is extended or adjusted under 35 U.S.C. 154(b) by 690 days.

(21) Appl. No.: 17/995,014

(22) PCT Filed: Jun. 8, 2021

(86) PCT No.: PCT/KR2021/007163

§ 371 (c)(1),
(2) Date: Sep. 29, 2022

(87) PCT Pub. No.: WO2021/251730

PCT Pub. Date: Dec. 16, 2021

(65) Prior Publication Data

US 2023/0210748 A1 Jul. 6, 2023

(30) Foreign Application Priority Data

Jun. 8, 2020 (KR) ........................ 10-2020-0068976

(51) Int. Cl.
*A61K 8/64* (2006.01)
*A61Q 19/08* (2006.01)
(Continued)

(52) U.S. Cl.
CPC ................ *A61K 8/64* (2013.01); *A61Q 19/08* (2013.01); *C07K 7/06* (2013.01); *C07K 7/08* (2013.01); *A61K 2800/91* (2013.01)

(58) Field of Classification Search
CPC ...... A61K 8/64; A61K 2800/91; A61Q 19/08; C07K 7/06; C07K 7/08
See application file for complete search history.

(56) References Cited

U.S. PATENT DOCUMENTS

2014/0328782 A1 11/2014 Chung et al.

FOREIGN PATENT DOCUMENTS

KR 1020040092448 5/2006
KR 1020110091923 3/2013
(Continued)

OTHER PUBLICATIONS

Bachem. Regentide-034 Molecular Weight. https://www.bachem.com/knowledge-center/peptide-calculator/ (Year: 2025).*
(Continued)

*Primary Examiner* — Jennifer A Berrios
*Assistant Examiner* — Chasity P Janosko
(74) *Attorney, Agent, or Firm* — MEDLER FERRO WOODHOUSE & MILLS PLLC

(57) ABSTRACT

The present invention relates to Regentide-034 and Regentide-041, and more particularly, to the use of a mixture of Regentide-034 and Regentide-041 for skin protection and wrinkle improvement. The mixture of Regentide-034 and Regentide-041 according to the present invention not only has no cytotoxicity, but also has remarkable effects of promoting cell proliferation, promoting collagen synthesis, inhibiting elastase activity, and inhibiting cell death caused by ultraviolet rays, and thus can be utilized in various ways in the fields of pharmacy, medicine, cosmetics, and food.

8 Claims, 10 Drawing Sheets

Specification includes a Sequence Listing.

(51) Int. Cl.

| | |
|---|---|
| ***C07K 7/06*** | (2006.01) |
| ***C07K 7/08*** | (2006.01) |

(56) References Cited

FOREIGN PATENT DOCUMENTS

| | | | | |
|---|---|---|---|---|
| KR | 1020150190292 | | 7/2017 | |
| KR | 1020170018875 | | 8/2018 | |
| WO | 2018044234 | A1 | 3/2018 | |
| WO | WO-2018151867 | A1 * | 8/2018 | ............. A61K 38/08 |

OTHER PUBLICATIONS

Bachem. Regentide-041 Molecular Weight. https://www.bachem.com/knowledge-center/peptide-calculator/ (Year: 2025).*

* cited by examiner

| Peptide | Efficacy(%)(Mean±SEM) |
|---|---|
| Regentide -034 (75 μM) & Regentide -041 (75 μM) | 36.4 ± 2.9 |

[Human skin dermal fibroblast]

COMPOSITION COMPRISING REGENTIDE-034 AND REGENTIDE-041 FOR SKIN CARE OR WRINKLE REDUCTION

TECHNICAL FIELD

The present invention relates to Regentide-034 and Regentide-041 and, more specifically, to a use of a mixture of Regentide-034 and Regentide-041 for improving skin conditions.

BACKGROUND ART

The skin is generally divided into the epidermis, dermis, and subcutaneous tissues. The dermis contains necessary appendages of the skin, such as blood vessels, lymphatic system, pores, and fibroblasts. It is a thick layer that is 15 to 40 times the thickness of the epidermis and occupies most of the skin. The dermal tissue consists of cross-linked fibers, collagen, and elastic fibers, elastin, which are synthesized in fibroblasts. Collagen is a long fiber that plays a role in supporting the body, binding it together, and forming the interface. Collagen plays a role in resisting pressure or external forces applied to the skin. On the other hand, elastin plays a role in maintaining the elasticity of the skin like a spring. Collagen and elastin form a network structure to maintain the elasticity of the skin.

As the skin ages, wrinkles form. As get older, the number, depth, and extent of wrinkles increases. Aging is divided into intrinsic and extrinsic aging. Intrinsic aging refers to the continuous decline in the structure and physiological function of the skin with age. Aging caused by external factors is induced by exposure to ultraviolet rays over a long period of time.

Collagen decreases with age and photoaging caused by UV irradiation, which is known to be closely related to the formation of wrinkles in the skin. In addition, collagen plays an important role in wound healing, and the synthesis of collagen in the damaged epithelium is promoted to quickly restore the wound without scarring. The main function of collagen is known to the firmness of the skin, the resistance and bonding of tissues, and the support of cell adhesion. Such collagen is known to be closely related to the formation of wrinkles in the skin in which the thickness of the skin becomes thinner due to aging and photoaging by UV irradiation.

It has been reported that elastase generated from fibroblasts plays an important role in the three-dimensional distortion of skin elastic fibers, and the increase in elastase activity contributes to the formation of skin wrinkles by reducing elastin and collagen in the skin. It is known that after UV irradiation, elastase activity increases so that the change in the elastase activity is the main cause of the decrease in skin elasticity and the formation of wrinkles due to UV rays.

DISCLOSURE

Technical Problem

Accordingly, the present inventors have completed the present invention by developing peptide Regentide-034 and 041 while searching for a novel skin improvement substance and confirming that a mixture thereof has an excellent skin improvement effect.

Therefore, it is an object of the present invention to provide a composition for skin condition improvement, the composition including: a peptide represented by the amino acid sequence of SEQ ID NO: 1; and a peptide represented by the amino acid sequence of SEQ ID NO: 2.

It is another object of the present invention to provide a method for treating a wound, the method including step of administrating to an individual in need thereof a peptide represented by the amino acid sequence of SEQ ID NO: 1 and a peptide represented by the amino acid sequence of SEQ ID NO: 2.

Technical Solution

In order to achieve the above object, the present invention provides a cosmetic composition for skin condition improvement, the composition including: a peptide represented by the amino acid sequence of SEQ ID NO: 1; and a peptide represented by the amino acid sequence of SEQ ID NO: 2.

In addition, the present invention provides a quasi-drug composition for skin condition improvement, the composition including: a peptide represented by the amino acid sequence of SEQ ID NO: 1; and a peptide represented by the amino acid sequence of SEQ ID NO: 2.

In addition, the present invention provides a food composition for skin condition improvement, the composition including: a peptide represented by the amino acid sequence of SEQ ID NO: 1; and a peptide represented by the amino acid sequence of SEQ ID NO: 2.

In addition, the present invention provides a health functional food composition for skin condition improvement, the composition including: a peptide represented by the amino acid sequence of SEQ ID NO: 1; and a peptide represented by the amino acid sequence of SEQ ID NO: 2.

In addition, the present invention provides a filler composition for skin condition improvement, the composition including: a peptide represented by the amino acid sequence of SEQ ID NO: 1; and a peptide represented by the amino acid sequence of SEQ ID NO: 2.

In addition, the present invention provides a filler for skin injection, the filler including: a peptide represented by the amino acid sequence of SEQ ID NO: 1; and a peptide represented by the amino acid sequence of SEQ ID NO: 2.

In addition, the present invention provides a pharmaceutical composition for wound treatment, the composition including: a peptide represented by the amino acid sequence of SEQ ID NO: 1; and a peptide represented by the amino acid sequence of SEQ ID NO: 2.

In addition, the present invention provides a method for treating wound, the method including step of administrating to an individual in need thereof a peptide represented by the amino acid sequence of SEQ ID NO: 1 and a peptide represented by the amino acid sequence of SEQ ID NO: 2.

Advantageous Effects

A mixture of Regentide-034 and Regentide-041 according to the present invention is free of cytotoxicity and has remarkable effects of promoting cell proliferation and collagen synthesis, inhibiting elastase activity, and suppressing ultraviolet light-induced cell death and as such, can be variously utilized in the pharmaceutical, medicinal, cosmetic, and food fields.

BEST MODE

Figure 1:
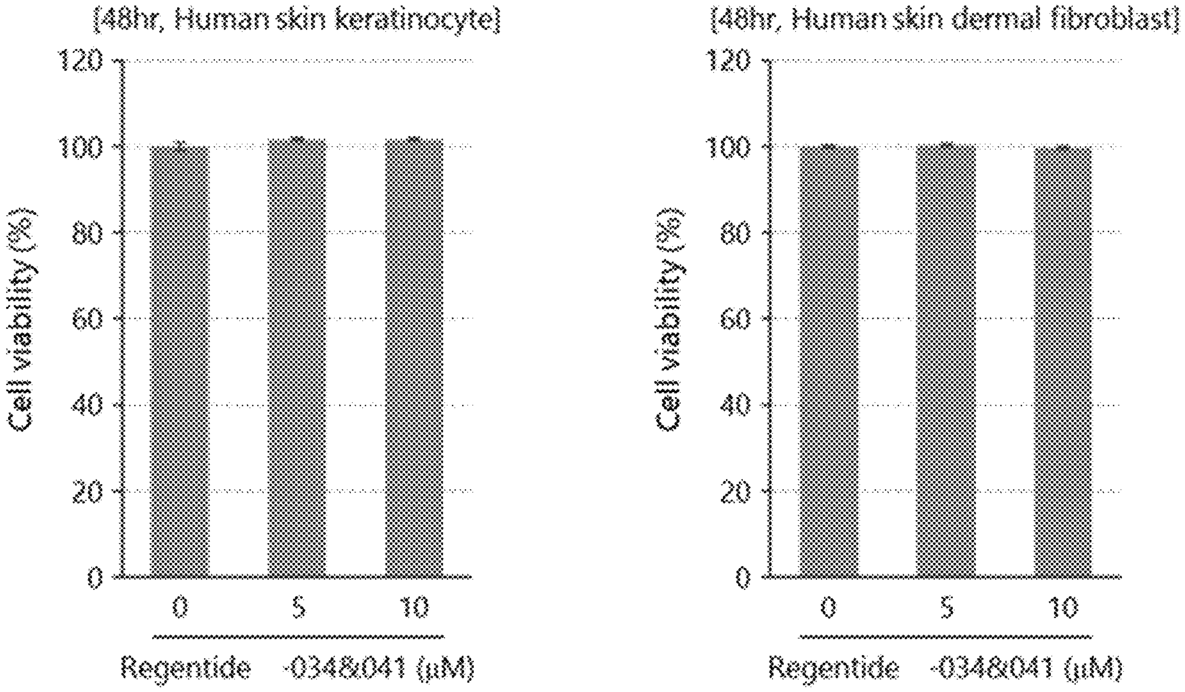
FIG. 1 is a view showing the results of confirming the cytotoxicity of a mixture of Regentide-034 and Regentide-041 according to the present invention.

Hereinafter, the present invention is described in detail.

According to an aspect of the present invention, the present invention provides a composition for skin condition improvement, the composition including: a peptide represented by the amino acid sequence of SEQ ID NO: 1; and a peptide represented by the amino acid sequence of SEQ ID NO: 2.

In the present invention, a peptide refers to a linear molecule formed by combining amino acid residues with each other by peptide bonds. The peptide may be prepared according to a chemical synthesis method known in the art, and preferably may be prepared according to a solid-phase synthesis technique but is not limited thereto.

In an embodiment of the present invention, the peptide represented by the amino acid sequence of SEQ ID NO: 1 or 2 preferably includes an amine group (—$NH_2$) conjugated to the C-terminus thereof, and peptides conjugated with amine groups are named 'Regentide-034' and 'Regentide-041,' respectively. The Regentide-034 may be represented by the amino acid sequence of SEQ ID NO: 3, and the Regentide-041 may be represented by the amino acid sequence of SEQ ID NO: 4. In Regentide-034 and Regentide-041, an amine group is conjugated to the C-terminus of the peptide represented by the amino acid sequence of SEQ ID NO: 1 or 2, thereby significantly improving stability in the tissue.

In an embodiment of the present invention, it is confirmed through an experiment that the peptide represented by the amino acid sequence of SEQ ID NO: 1; and the peptide represented by the amino acid sequence of SEQ ID NO: 2; has no cytotoxicity to epidermal keratinocytes and fibroblasts, and has a significant cell proliferation promotion, collagen synthesis promotion and cell migration promoting effect.

The scope of the present invention includes functional equivalents of a peptide represented by the amino acid sequence of SEQ ID NO: 1; and a peptide represented by the amino acid sequence of SEQ ID NO: 2.

In the present invention, functional equivalents include those having 80% or more, preferably 90%, more preferably 95% or more sequence homology (i.e., identity) with an amino acid sequence represented by SEQ ID NO: 1 or 2 as a result of addition, substitution, or deletion of amino acid, for example, those having 80%, 81%, 82%, 83%, 84%, 85%, 86%, 87%, 88%, 89%, 90%, 91%, 92%, 93%, 94%, 95%, 96%, 97%, 98%, 99%, or 100% sequence homology with the amino acid sequence. It refers to a peptide that exhibits substantially the same physiological activity of a peptide represented by the amino acid sequence of SEQ ID NO: 1; and a peptide represented by the amino acid sequence of SEQ ID NO: 2. In addition, as for the peptide represented by the amino acid sequence of SEQ ID NO: 1 and the peptide represented by the amino acid sequence of SEQ ID NO: 2 of the present invention, proteins having its native amino acid sequence as well as amino acid sequence variants thereof are also included within the scope of the present invention. The variant of the peptide represented by the amino acid sequence of SEQ ID NO: 1 and the peptide represented by the amino acid sequence of SEQ ID NO: 2 refers to a peptide having a sequence different from the natural amino acid sequence of the peptide by deletion, insertion, non-conservative or conservative substitution, or a combination thereof, of one or more amino acid residues. Amino acid exchanges in proteins and peptides that do not entirely alter the activity of the molecule are known in the art. The peptide represented by the amino acid sequence of SEQ ID NO: 1 or a variant thereof may be extracted from nature or prepared by a synthetic method or genetic recombination method based on a DNA sequence.

In addition, sequence homology may be determined by standard methods that are commonly used to compare similar portions of the amino acid sequences constituting the peptide. Using a computer program such as Basic Local Alignment Search Tool (BLAST®) or FASTA, at least two polypeptides are aligned for optimal matching of their respective amino acids (either along the full length of one or both sequences or along a predetermined portion of one or both sequences). The programs provide a default opening penalty and a default gap penalty, and a scoring matrix such as PAM 250 (a standard scoring matrix) may be used in conjunction with the computer program. For example, the percent homology may be calculated as: the total number of identical matches multiplied by 100 and then divided by the sum of the length of the longer sequence within the matched span and the number of gaps introduced into the longer sequences in order to align the two sequences.

In the present invention, substantially homogeneous physiological activity means skin condition improvement activity, and more specifically, means one or more kinds of the selected activities from the group consisting of skin aging improvement, skin regeneration, skin elasticity improvement, skin wrinkle prevention, skin wrinkle improvement and skin wound regeneration.

In addition, the scope of the functional equivalents also encompasses derivatives obtained by modifying a part of the chemical structure of the constituting amino acid while maintaining the basic framework and skin condition improvement activity of the peptide represented by the amino acid sequence of SEQ ID NO: 1. For example, this includes structural modifications for altering the stability, storage, volatility, or solubility of the protein.

In the present invention, "improvement" refers to any action that at least reduces a parameter related to alleviation or treatment of a condition, for example, the severity of a symptom.

"Skin condition improvement" according to the present invention may be at least one kind of activity selected from the group consisting of skin aging improvement, skin regeneration, skin elasticity improvement, skin wrinkle prevention, skin wrinkle improvement, and skin wound regeneration.

In the present invention, "skin aging" refers to all diseases caused by an increase in active oxygen, and non-limiting examples of the skin aging include wrinkles, sagging skin, reduced elasticity, and the like.

In the present invention, "skin regeneration," "skin elasticity improvement" or "skin wrinkle prevention or improvement" refers to any action that increases the total amount of collagen by inhibiting collagenase activity.

In the present invention, "skin wound regeneration" refers to any action that regenerates damaged skin due to cuts, etc. by increasing the number of skin cells and promoting skin cell migration ability.

In an embodiment of the present invention, the skin aging is photoaging or natural aging, but the scope of the present invention is not limited by the cause of skin aging.

In an embodiment of the present invention, the concentration of the peptide is preferably 0.1 μM to 1,000 μM.

In an embodiment of the present invention, the peptide represented by the amino acid sequence of SEQ ID NO: 1; and the peptide represented by the amino acid sequence of SEQ ID NO: 2; may be preferably mixed in a concentration ratio of 1:0.1 to 10, and more preferably in a concentration ratio of 1:1.

In an embodiment of the present invention, the cosmetic composition is preferably formulated in a filler, but is not limited thereto.

The composition for skin condition improvement according to the present invention may be a cosmetic composition, a quasi-drug composition, a food composition, a health functional food composition, or a filler composition.

When the composition for skin condition improvement according to the present invention is a cosmetic composition, the cosmetic composition of the present invention may further include conventional adjuvants and carriers such as antioxidants, stabilizers, solubilizers, vitamins, pigments, fragrances, and the like, which are commonly used in cosmetic compositions in addition to the active ingredients. For example, the cosmetic composition may further include auxiliary components such as glycerin, butylene glycol, polyoxyethylene hydrogenated castor oil, tocopheryl acetate, citric acid, panthenol, squalane, sodium citrate, and allantoin.

Since the cosmetic composition of the present invention is basically applied to the skin, it may be prepared in any formulation conventionally prepared with reference to a cosmetic composition in the art. For example, it may be formulated as a solution, a suspension, an emulsion, a paste, a gel, a cream, a lotion, a powder, a soap, a surfactant-containing cleanser, an oil, a powder foundation, an emulsion foundation, a wax foundation, and a spray, etc., but is not limited thereto. More specifically, it may be prepared in the form of a flexible lotion, a nourishing lotion, a nourishing cream, a massage cream, an essence, an eye cream, a cleansing cream, a cleansing foam, a cleansing water, a mask pack, a spray, or a powder.

When the formulation of the present invention is a paste, cream or gel, animal oil, vegetable oil, wax, paraffin, starch, tragacanth, cellulose derivative, polyethylene glycol, silicone, bentonite, silica, talc, zinc oxide, etc. may be included as carrier components.

When the formulation of the present invention is a powder or a spray, lactose, talc, silica, aluminum hydroxide, calcium silicate or polyamide powder may be used as a carrier component. In particular, in the case of a spray, the carrier component may additionally include a propellant such as chlorofluorohydrocarbon, propane/butane or dimethyl ether.

When the formulation of the present invention is a solution or emulsion, a solvent, a solubilizer or an emulsifier may be included as a carrier component, and in particular, it includes water, ethanol, isopropanol, ethyl carbonate, ethyl acetate, benzyl alcohol, benzyl benzoate, propylene glycol, 1,3-butyl glycol oil, glycerol aliphatic ester, polyethylene glycol or fatty acid esters of sorbitan, etc.

When the formulation of the present invention is a suspension, as the carrier component, a liquid diluent such as water, ethanol or propylene glycol, a suspension such as ethoxylated isostearyl alcohol, polyoxyethylene sorbitol ester and polyoxyethylene sorbitan ester, microcrystalline cellulose, aluminum metahydroxide, bentonite, agar or tragacanth, and the like may be included.

When the formulation of the present invention is a surfactant-containing cleansing, as the carrier component, aliphatic alcohol sulfate, aliphatic alcohol ether sulfate, sulfosuccinic acid monoester, isethionate, imidazolinium derivative, methyltaurate, sarcosinate, fatty acid amide ether sulfate, alkylamidobetaine, aliphatic alcohol, fatty acid glyceride, fatty acid diethanolamide, a vegetable oil, lanolin derivative, ethoxylated glycerol fatty acid ester and the like may be included.

The composition for skin condition improvement according to the present invention may be a quasi-drug composition.

In the present invention, quasi-drugs refer to products with a milder action than pharmaceuticals among articles used for the purpose of diagnosing, treating, improving, alleviating, treating, or preventing diseases of humans or animals. For example, according to the Korean Pharmaceutical Affairs Act, quasi-drugs include products used for the treatment or prevention of diseases in humans and animals, and products with minor or no direct action on the human body without products used for pharmaceutical purposes.

The quasi-drug composition of the present invention may be prepared as one selected from the group consisting of body cleanser, foam, soap, mask, ointment, cream, lotion, essence, and spray, but is not limited thereto.

In the quasi-drug composition of the present invention, description of the peptide represented by the amino acid sequence of SEQ ID NO: 1, skin regeneration, skin elasticity improvement, skin wrinkle prevention or improvement, skin aging prevention or improvement, skin inflammation improvement and skin whitening improvement is the same as described above with respect to the cosmetic composition.

The food composition for skin condition improvement according to the present invention may be used as a health functional food, food additive or dietary supplement.

When the peptide represented by the amino acid sequence of SEQ ID NO: 1; and the peptide represented by the amino acid sequence of SEQ ID NO: 2; are used as a food additive, the mixture may be added as it is, or may be suitably used according to a conventional method, such as mixed with other foods or food ingredients.

In addition, the mixing amount of the peptide represented by the amino acid sequence of SEQ ID NO: 1; and the peptide represented by the amino acid sequence of SEQ ID NO: 2; may be suitably changed depending on the purpose of use (prevention, health, or therapeutic treatment). In addition, the mixture is preferably included in an amount of 0.01 to 95% by weight based on the total weight of the food composition and more preferably, it is included in an amount of 1 to 80% by weight. When the content is less than 0.01% by weight, the antioxidant or anti-inflammatory effect may be insignificant, and when it exceeds 95% by weight, the effect increase rate is low compared to the amount used, which may be uneconomical.

As a specific example, when preparing food or beverage, the peptide represented by the amino acid sequence of SEQ ID NO: 1; and the peptide represented by the amino acid sequence of SEQ ID NO: 2 of the present invention; are added in an amount of 15% by weight or less, preferably 10% by weight or less, based on the raw material. However, when it is consumed for a long period of time for health and hygiene purposes or for health control, it may be added in an amount less than the above range, and since there is no problem in terms of safety, the active ingredient may be used in an amount above the above range.

The type of food is not particularly limited, but examples of foods that may be added with a peptide represented by the amino acid sequence of SEQ ID NO: 1; and a peptide represented by the amino acid sequence of SEQ ID NO: 2; of the present invention include meat, sausage, bread, chocolate, candy, snacks, confectionery, pizza, ramen, other noodles, gum, dairy products including ice cream, various soups, beverages, teas, drinks, alcoholic beverages, vitamin complexes, etc., and includes all health foods in the ordinary meaning.

When the food composition of the present invention is prepared as a beverage, it may contain additional ingredients such as various flavoring agents or natural carbohydrates like conventional beverages. Examples of the natural carbohydrate include monosaccharides such as glucose and fructose; disaccharides such as maltose and sucrose; natural sweeteners such as dextrin and cyclodextrin; and synthetic sweeteners such as saccharin and aspartame. The natural carbohydrate is included in an amount of 0.01 to 10% by weight, preferably 0.01 to 0.1% by weight, based on the total weight of the food composition of the present invention.

The food composition of the present invention includes various nutrients, vitamins, electrolytes, flavoring agents, colorants, pectic acid and salts thereof, alginic acid and salts thereof, organic acids, protective colloidal thickeners, pH adjusters, stabilizers, preservatives, glycerin, alcohol, carbonation agent used in carbonic acid beverages and may include flesh for the production of natural fruit juice, fruit juice beverages and vegetable beverages, but is not limited thereto. These components may be used independently or in combination. The additive ratio is not particularly limited, but it is preferably included in the range of 0.01 to 0.1% by weight based on the total weight of the food composition of the present invention.

In the case of long-term intake for the purpose of health and hygiene or health control, the food composition of the present invention may be taken for a long period of time because there is no problem in terms of safety.

The composition for skin condition improvement according to the present invention may be a filler composition.

In the present invention, a filler refers to an injectable substance that replenishes skin tissue such as improving wrinkles and restoring aesthetic volume by injecting a biocompatible material intradermally or subcutaneously. Recently, the filler includes not only skin-like substances, but also substances that promote the proliferation of cells in the skin, substances that promote the production of collagen, and the like. By filler treatment, wrinkles are smoothed out in a short time, thin lips are thickened, and pitted scars are filled. Currently, as a substance for manufacturing a filler approved by FDA or MFDS, there are collagen, hyaluronic acid, calcium hydroxylapatite, polylactic acid, and the like.

In a preferred example of the present invention, the filler composition of the present invention may include collagen, hyaluronic acid, calcium hydroxylapatite, and polylactic acid.

In addition, the filler composition of the present invention may be formulated in a powder form, more specifically in a freeze-dried powder form, in order to provide ease of use and storage stability. Meanwhile, before injection into the skin, it is required to have a pre-treatment step of solubilizing by dissolving in an aqueous medium such as PBS. However, the solubilized filler composition may be directly applied depending on storage and formulation conditions.

In an embodiment of the present invention, in order to impart an effective skin regeneration effect, the filler composition of the present invention may further include a cell growth factor or a vitamin. The cell growth factor is a generic term for polypeptides that promote cell division, growth, and differentiation and may be preferably selected from the group consisting of fibroblast growth factor (FGF), epidermal growth factor (EGF), keratinocyte growth factor (KGF), transforming growth factor alpha (TGF-α), transforming growth factor beta (TGF-β), granulocyte formation stimulating factor (GCSF), insulin-like growth factor (IGF), vascular endothelial growth factor (VEGF), hepatocyte growth factor (HGF), platelet-derived growth factor-BB (PDGFBB), brain-derived neurotrophic factor (BDNF), and glial cell-derived neurotrophic factor (GDNF), and the cell growth factor may be contained in a concentration of 20 ng/ml to 20 μg/ml, but is not limited thereto.

In order to relieve pain during the injection process, the filler composition of the present invention may further include a local anesthetic. The local anesthetic may be selected from the group consisting of ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, ethyl chloride, etidocaine, betaeucaine, euprocin, fenalcomine, formocaine, hexylcaine, hydroxyteteracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propicocaine, propoxycaine, psuedococaine, pyrrocaine, ropivacaine, bupivacaine, salicyl alcohol, tetracaine, tolycaine, trimecaine, zolamine and salts thereof, and the amount of the anesthetic agent is preferably 0.1% by weight to 5.0% by weight, more preferably 0.2% by weight to 1.0% by weight, based on the total weight of the filler composition, but it is not limited thereto.

In order to prevent oxidation and decomposition of the hydrogel produced by gelation in the body, the filler composition of the present invention may further include an antioxidant. The antioxidant may be selected from the group consisting of polyol, mannitol, and sorbitol, and the amount of the antioxidant may be contained in preferably 0.1% by weight to 5.0% by weight, more preferably 0.2% by weight to 1.0% by weight, based on the total weight of the filler composition, but is not limited thereto.

According to another aspect of the present invention, the present invention provides a filler for skin injection including a peptide represented by the amino acid sequence of SEQ ID NO: 1; and a peptide represented by the amino acid sequence of SEQ ID NO: 2.

In an embodiment of the present invention, the peptide represented by the amino acid sequence of SEQ ID NO: 1 or 2 has preferably an amine group (—$NH_2$) conjugated to the C-terminus. Peptides conjugated with amine groups were named 'Regentide-034' and 'Regentide-041,' respectively. The Regentide-034 may be represented by the amino acid sequence of SEQ ID NO: 3, and the Regentide-041 may be represented by the amino acid sequence of SEQ ID NO: 4. The Regentide-034 and Regentide-041, respectively, are the peptide represented by the amino acid sequence of SEQ ID NO: 1 or 2 conjugated with an amine group at the C-terminus, thereby significantly improving stability in the tissue.

In an embodiment of the present invention, the filler is for skin condition improvement, which is preferably at least one kind selected from the group consisting of skin aging improvement, skin regeneration, skin elasticity improvement, skin wrinkle prevention, skin wrinkle improvement and skin wound regeneration, but is not limited thereto.

In an embodiment of the present invention, the filler is preferably for injection, but the scope of the present invention is not limited thereto.

According to another aspect of the present invention, the present invention provides a pharmaceutical composition for wound treatment including a peptide represented by the amino acid sequence of SEQ ID NO: 1; and a peptide represented by the amino acid sequence of SEQ ID NO: 2.

In an embodiment of the present invention, the peptide represented by the amino acid sequence of SEQ ID NO: 1 or 2 has preferably an amine group (—$NH_2$) conjugated to the C-terminus. Peptides conjugated with amine groups were named 'Regentide-034' and 'Regentide-041,' respectively. The Regentide-034 may be represented by the amino acid sequence of SEQ ID NO: 3, and the Regentide-041 may be represented by the amino acid sequence of SEQ ID NO: 4. The Regentide-034 and Regentide-041, respectively, are the peptide represented by the amino acid sequence of SEQ ID NO: 1 or 2 having an amine group conjugated to the C-terminus, thereby significantly improving stability in the tissue.

In the present invention, "wound treatment" refers to the action of treating the damaged site (i.e., wound) by increasing the number of cells and promoting cell migration ability in the damaged area due to cuts or the like.

The pharmaceutical composition for wound treatment of the present invention may be formulated and used in various forms according to conventional methods, respectively. For example, it may be formulated in oral dosage forms such as a powder, a granule, a tablet, a capsule, a suspension, an emulsion, and a syrup, and may be formulated in the form of an external preparation, a suppository, and a sterile injection solution. However, it may be most preferable that the composition of the present invention is provided in the form of an external preparation for skin. Specifically, it may be used in the form of a liquid, ointment, cream, lotion, spray, patch, gel or aerosol.

In addition, it may further include a pharmaceutically acceptable carrier, excipient and diluent according to each formulation. In addition, according to a conventional method, it may be formulated and used in the form of a powder, a granule, a tablet, a capsule, a suspension, an emulsion, a syrup, an external preparation such as an aerosol, and a sterile injection solution, preferably a cream, a gel, a patch, a spray, an ointment, an oral preparation, a lotion, liniment, paste, or cataplasma formulation. For example, in the case of an external skin preparation used locally in the relevant area, it may include conventional additives, for example, a preservative, a solvent that aids in drug penetration, and an emollient in the case of ointments and creams and may contain conventional carriers such as ethanol or oleyl alcohol. Suitable formulations known in the art are preferably those disclosed in the document (Remington's Pharmaceutical Science, recently Mack Publishing Company, Easton PA), but are not limited thereto.

The carrier, excipient and diluent include lactose, dextrose, sucrose, oligosaccharide, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxy benzoate, propyl hydroxy benzoate, talc, magnesium stearate, mineral oil, and the like. When the pharmaceutical composition is prepared or formulated, it is prepared using a commonly used diluent or excipient such as a filler, an extender, a binder, a wetting agent, a disintegrant, and a surfactant. Solid preparations for oral administration include a tablet, a pill, a powder, a granule, a capsule, etc., and these solid preparations are prepared by mixing at least one excipient in the composition, for example, starch, calcium carbonate, sucrose, lactose, gelatin, and the like. Further, in addition to a simple excipient, a lubricant such as magnesium stearate and talc are also used. Liquid formulations for oral use include a suspension, a solution, an emulsion, and a syrup. In addition to a commonly used simple diluent such as water and liquid paraffin, various excipients such as a wetting agent, a sweetener, a fragrance, and a preservative may be included. Formulations for parenteral administration include a sterile aqueous solution, a non-aqueous solution, a suspension, an emulsion, a freeze-dried preparation, a suppository, and the like. Non-aqueous solvents and suspensions include propylene glycol, polyethylene glycol, vegetable oils such as olive oil, and injectable esters such as ethyl oleate. As the base of the suppository, witepsol, macrogol, tween 61, cacao butter, laurin, glycerogelatin, and the like may be used. The above ingredients may be added independently or in combination to the active ingredient, that is, the pharmaceutical composition.

In the present invention, administration means providing the pharmaceutical composition of the present invention to an individual by any suitable method.

The pharmaceutical composition of the present invention may be administered in an amount of an active ingredient or pharmaceutical composition that induces a biological or medical response in a tissue system, animal or human as considered by a researcher, veterinarian, physician or another clinician, that is, in a therapeutically effective amount, which is an amount that induces alleviation of symptoms of the disease or disorder to be treated. It is apparent to those skilled in the art that the therapeutically effective dosage and frequency of administration for the pharmaceutical composition of the present invention varies depending on the desired effect. Therefore, the optimal dosage to be administered may be easily determined by those skilled in the art, and may be adjusted according to various factors including type of disease, the severity of the disease, the content of the active ingredient and other components contained in the composition, the type of formulation, the age, weight, general health status, gender and diet of the patient, the administration time, the route of administration and secretion rate of the composition, treatment period, and concurrently used drugs.

The pharmaceutical composition of the present invention may be administered in an amount of 1 to 10,000 mg/kg/day, preferably 1 to 200 mg/kg/day, and may be administered once a day, or may be administered in several divided doses.

According to another aspect of the present invention, the present invention provides a method for wound treatment including administering to an individual in need thereof a peptide represented by the amino acid sequence of SEQ ID NO: 1; and a peptide represented by the amino acid sequence of SEQ ID NO: 2.

In an embodiment of the present invention, the individual is an individual with a scar; or a wounded individual, but is not limited thereto.

A duplicate description is excluded in consideration of the complexity of the present specification, and terms not defined otherwise in the present specification have the meanings commonly used in the art to which the present invention pertains.

MODES OF THE INVENTION

Hereinafter, the present invention is described in more detail through examples. These examples are only for illustrating the present invention, and it will be apparent to those of ordinary skill in the art that the scope of the present invention is not to be construed as being limited by these examples.

Example 1. Synthesis of Peptide

A peptide for skin protection and wrinkle improvement was synthesized. The synthesized peptide is represented by the amino acid sequence of SEQ ID NO: 1 or 2, respectively, and an amine group (—$NH_2$) was conjugated to the C-terminus of each peptide for tissue safety. The peptide having an amine group conjugated to the C-terminus is represented by the amino acid sequence of SEQ ID NO: 3 or 4, respectively, and the peptide having an amine group conjugated to the C-terminus was named 'Regentide-034' and 'Regentide-041', respectively.

TABLE 1

| Name | SEQ ID NO. | Amino acid sequence |
|---|---|---|
| peptide-034 | 1 | AYGCYCGWGG |
| peptide-041 | 2 | CIPRGGICLVAL |
| Regentide-034 | 3 | AYGCYCGWGG-$NH_2$ |
| Regentide-041 | 4 | CIPRGGICLVAL-$NH_2$ |

In the Examples to be described later, experiments were conducted using a mixture of Regentide-034 (SEQ ID NO: 3) and Regentide-041 (SEQ ID NO: 4) in a concentration ratio of 1:1.

Example 2. Cytotoxicity Evaluation of a Mixture of Regentide-034 and Regentide-041

In order to confirm the cytotoxicity of the mixture of Regentide-034 and Regentide-041, the cytotoxicity was measured in HaCaT cells, which are human epidermal keratinocytes, and CCD-986Sk, which are human fibroblasts. In a 96-well plate, keratinocytes were seeded at $3\times10^3$ cells/well and fibroblasts were seeded at $5\times10^3$ cells/well, and then they were cultured in a medium containing 10% FBS in the cell culture conditions for 24 hours. After culture, 5 μM or 10 μM of a mixture of Regentide-034 and Regentide-041 was added to a medium without FBS, and they were cultured for 48 hours. Thereafter, 10 μl of CCK8 reaction solution (Dojindo Molecular Technologies, Kumamoto, Japan) was treated in each well, and they were reacted for 4 hours. Then, their absorbances were measured at 450 nm. The average absorbance value for each sample group was obtained. They were compared with the absorbance values of cells not treated with a mixture of Regentide-034 and Regentide-041 as controls to assess cell viability. The cell viability evaluation result is shown in FIG. 1.

As shown in FIG. 1, it was confirmed that the mixture of Regentide-034 and Regentide-041 had no cytotoxicity.

Example 3. Confirmation of Collagen Synthesis Effect of a Mixture of Regentide-034 and Regentide-041

3-1. Preventing the Decrease in Collagen Biosynthesis Performance Due to Photoaging To investigate the effect of preventing collagen biosynthesis decrease due to photoaging by a mixture of Regentide-034 and Regentide-041, CCD-986Sk, which are fibroblasts, were seeded in a 6-well plate at $2\times10^5$ cells/well, and then cultured in cell culture conditions for 24 hours in a medium containing 10% FBS. The medium was then discarded, and they were washed with 1×DPBS (Dulbecco's phosphate-buffered saline). Then, 500 μl of 1×DPBS was added, and UVB of 25 mJ/$cm^2$ was irradiated to the experimental group. Thereafter, a mixture of Regentide-034 and Regentide-041 was added to a medium without FBS at various concentrations (0, 0.1, 0.2, or 0.5 μM), and they were cultured in cell culture conditions for 24 hours. The cultured medium was recovered for each time period. The amount of procollagen secreted into the medium was measured with an absorbance of 450 nm using a procollagen ELISA Kit (R&D Systems, Inc., Minneapolis, Minn., USA) to calculate the amount. The results of confirming the improvement effect on the reduction of collagen biosynthesis performance due to photoaging by the mixture of Regentide-034 and Regentide-041 are shown in FIG. 2.

Figure 2:
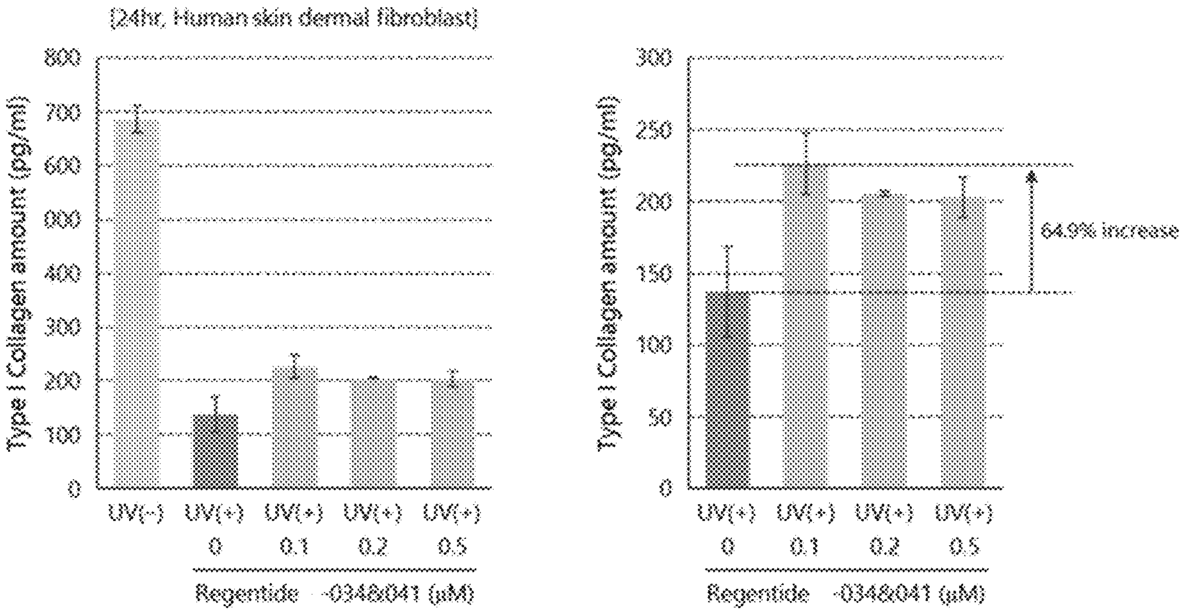
FIG. 2 is a view showing the results of confirming the improvement effect on collagen biosynthesis performance reduction due to photoaging of a mixture of Regentide-034 and Regentide-041 according to the present invention.

As shown in FIG. 2, it was confirmed that the collagen synthesis ability was reduced by 80% in the UVB-treated group after 24 hours of treatment with a mixture of Regentide-034 and Regentide-041. In addition, it was confirmed that when the mixture of Regentide-034 and Regentide-041 was treated, the collagen synthesis ability decreased by UVB was increased in all groups treated with the mixture of Regentide-034 and Regentide-041 compared to the group treated only with UVB. In particular, it was confirmed that the collagen synthesis ability was increased by 64.9% compared to the control group in the group treated with 0.2 μM of a mixture of Regentide-034 and Regentide-041.

3-2. Preventing the Decrease in Collagen Biosynthesis Performance Due to Natural Aging To investigate the effect of preventing collagen biosynthesis decrease due to natural aging by a mixture of Regentide-034 and Regentide-041, CCD-986Sk, which are fibroblasts, were subcultured and passage 15 and passage 20 cells were seeded in 6 well plates at $3\times10^5$ cells/well, and then cultured in cell culture conditions for 24 hours in a medium containing 10% FBS. The medium was then discarded, and they were washed with 1×DPBS (Dulbecco's phosphate-buffered saline). Thereafter, a mixture of Regentide-034 and Regentide-041 was added to a medium without FBS at various concentrations (0, 0.1, 0.2, or 0.5 μM), and they were cultured in cell culture conditions for 24 hours. The cultured medium was recovered for each time period. The amount of procollagen secreted into the medium was measured with an absorbance of 450 nm using a procollagen ELISA Kit (R&D Systems, Inc., Minneapolis, MN, USA) to calculate the amount. The results of confirming the improvement effect on the reduction of collagen biosynthesis performance due to natural aging by the mixture of Regentide-034 and Regentide-041 are shown in FIG. 3.

Figure 3:
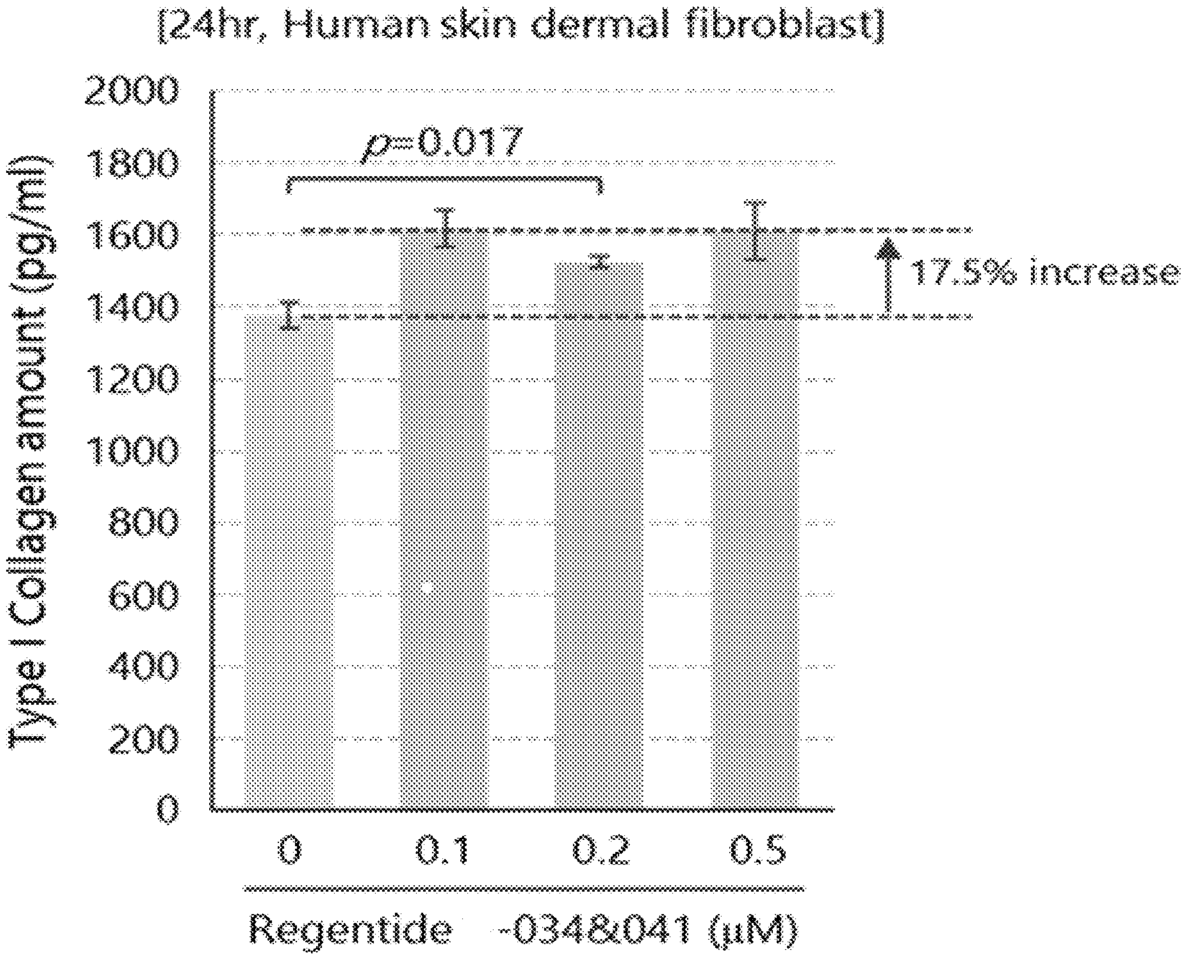
FIG. 3 is a view showing the results of confirming the improvement effect on collagen biosynthesis performance reduction due to natural aging of the mixture of Regentide-034 and Regentide-041 according to the present invention.

As shown in FIG. 3, after 24 hours of treatment with a mixture of Regentide-034 and Regentide-041, it was confirmed that the collagen synthesis ability was increased in all groups treated with a mixture of the Regentide-034 and Regentide-041 compared to the group not treated with a mixture of the Regentide-034 and Regentide-041. In particular, it was confirmed that the collagen synthesis ability was increased by 17.5% in the treatment group of 0.2 μM mixture of the Regentide-034 and Regentide-041.

Example 4. Inhibitory Effect of a Mixture of Regentide-034 and Regentide-041 on Elastase Activity In order to confirm the inhibitory ability of the mixture of Regentide-034 and Regentide-041 on elastase activity, it was measured using the Neutrophil Elastase colorimetric method (BML-AK497-001, Enzo Life Sciences™ Neutrophil Elastase colorimetric assay kit, Pennsylvania, USA). First, the assay buffer was diluted with D.W. in a ratio of 1:1, and then the elastase reagent and the substrate reagent were diluted to have final concentrations of 2.2 μU/ml and 100 μM, respectively. Then, they were mixed with Regentide-034 and Regentide-041 at 75 μM and diluted to a final concentration of 150 μM. Working solution was prepared by mixing assay buffer; elastase reagent; and a mixture of Regentide-034 and Regentide-041. 95 μM of the working solution was added to a 96-well plate and reacted at 37° C. for 5 minutes. Next, 5 μM of substrate reagent was added, and absorbance was measured for 15 minutes at an absorbance at 405 nm with a microplate reader (Epoch 2 Microplate spectrophotometer. Biotek™ Microplate reader, Winooski, VT, USA). The results of confirming the effect of inhibiting elastase activity are shown in FIG. 4.

Figure 4:
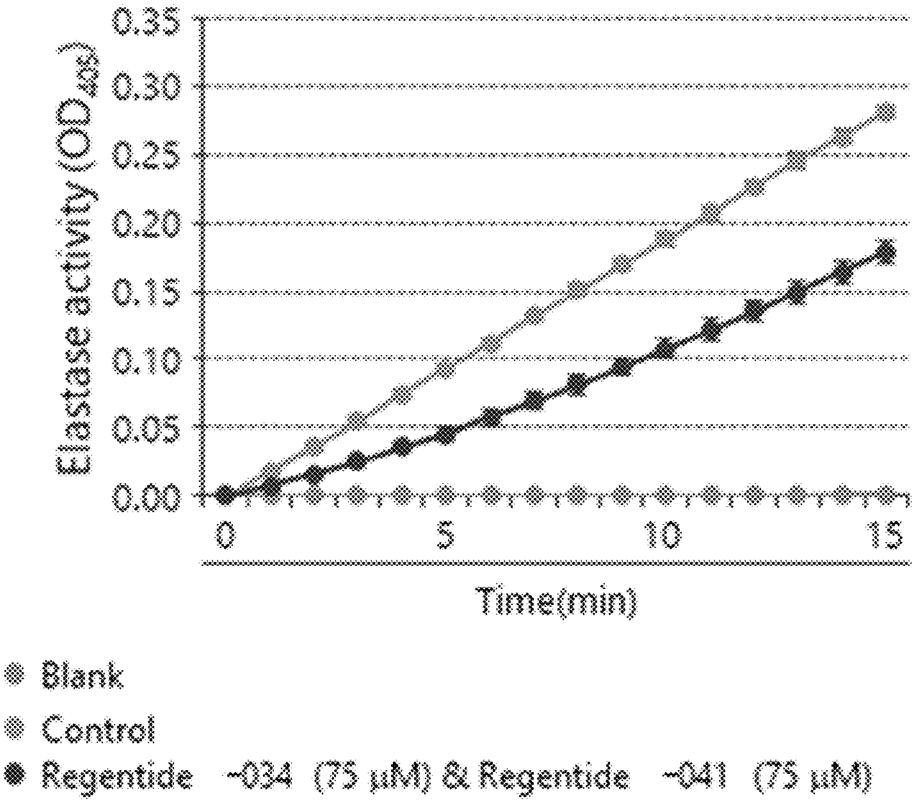
FIG. 4 is a view showing the results of confirming the elastase activity inhibitory ability of the mixture of Regentide-034 and Regentide-041 according to the present invention.

As shown in FIG. 4, it was confirmed that the mixture of Regentide-034 and Regentide-041 had excellent elastase inhibitory efficacy. More specifically, it was confirmed that the group treated with the mixture of Regentide-034 and Regentide-041 had the elastase activity inhibitory efficacy of 36.4±2.95%.

Example 5. Cell Growth Promoting Efficacy of the Mixture of Regentide-034 and Regentide-041

5-1. Efficacy of Promoting Epidermal Keratinocyte Growth

To check the cell proliferative ability of the mixture of the Regentide-034 and Regentide-041, HaCaT cells, epidermal keratinocytes, were seeded in a 6-well plate at $1\times10^4$ cells/well and cultured in cell culture conditions for 6 hours in a medium containing 10% FBS. Thereafter, a mixture of Regentide-034 and Regentide-041 was added at various concentrations (100, 200, or 500 nM), and they were cultured for 8 days. The medium containing a mixture of Regentide-034 and Regentide-041 at various concentrations was replaced every day, and the cell number was counted every two days. The cell number measurement result is shown in FIG. 5.

Figure 5:
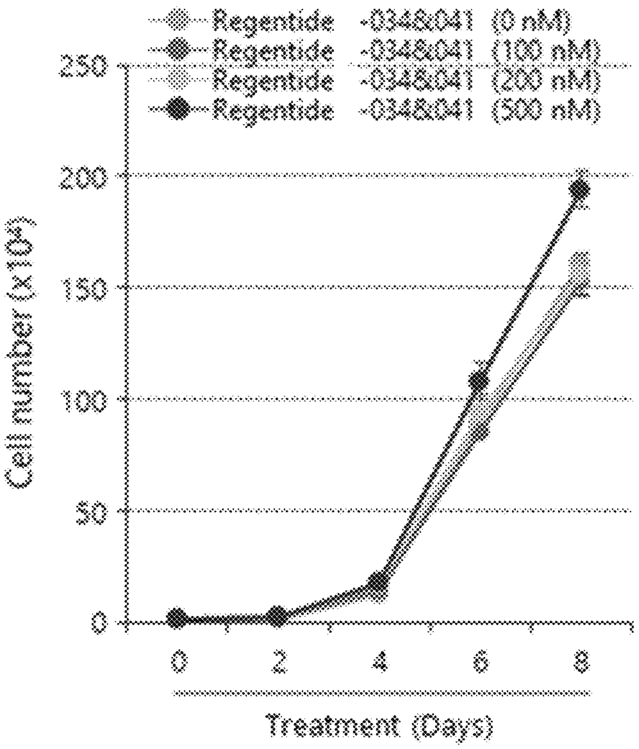
FIG. 5 is a view showing the results of confirming the epidermal keratinocyte growth promoting efficacy of a mixture of Regentide-034 and Regentide-041 according to the present invention.
Figure 5:
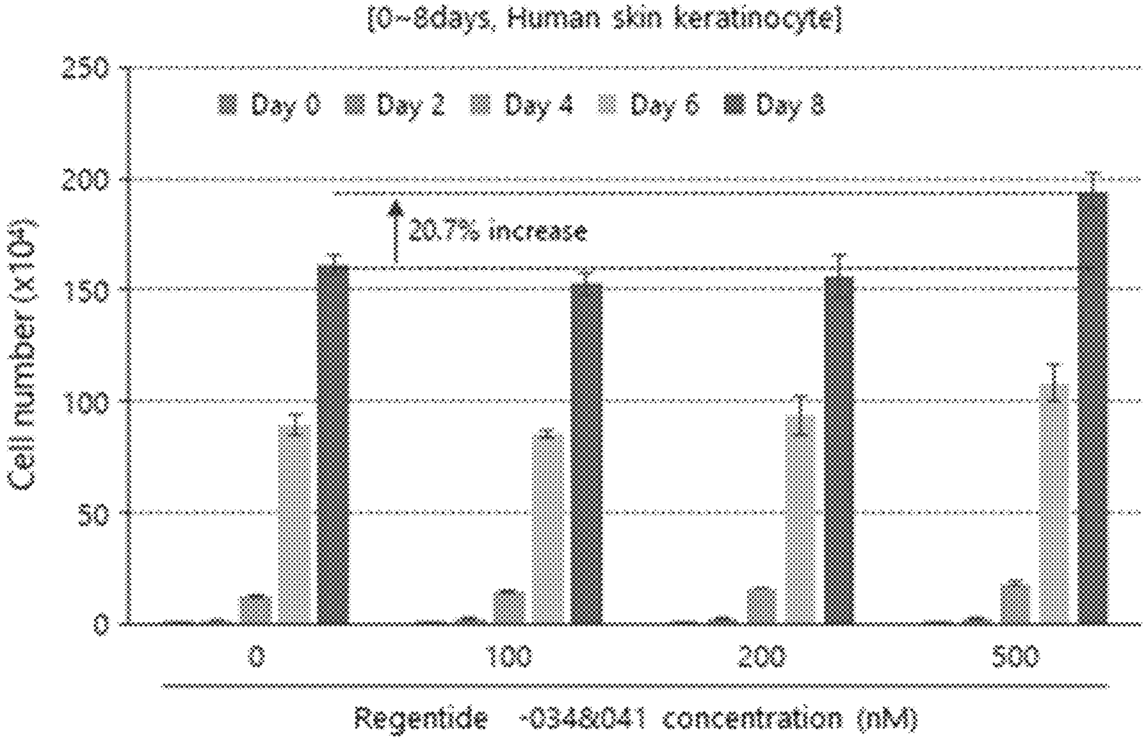

As shown in FIG. 5, it was confirmed that the group treated with the mixture of Regentide-034 and Regentide-041 promoted the growth of epidermal keratinocytes in a concentration and time-dependent manner. In particular, after 8 days of treatment with the mixture of Regentide-034 and Regentide-041, it was confirmed that the cell growth rate of the group treated with the mixture at 500 nM was about 20.7% higher than that of the control group.

5-2. Efficacy of Promoting Fibroblast Growth

To check the cell proliferative ability of the mixture of the Regentide-034 and Regentide-041, CCD986Sk cells, which are fibroblasts, were seeded in a 6-well plate at $1\times10^4$ cells/well and cultured in cell culture conditions for 6 hours in a medium containing 10% FBS. Thereafter, a mixture of Regentide-034 and Regentide-041 was added at various concentrations (100, 200, or 500 nM), and they were cultured for 8 days. The medium containing a mixture of Regentide-034 and Regentide-041 at various concentrations was replaced every day, and the cell number was counted every two days. The cell number measurement result is shown in FIG. 6.

Figure 6:
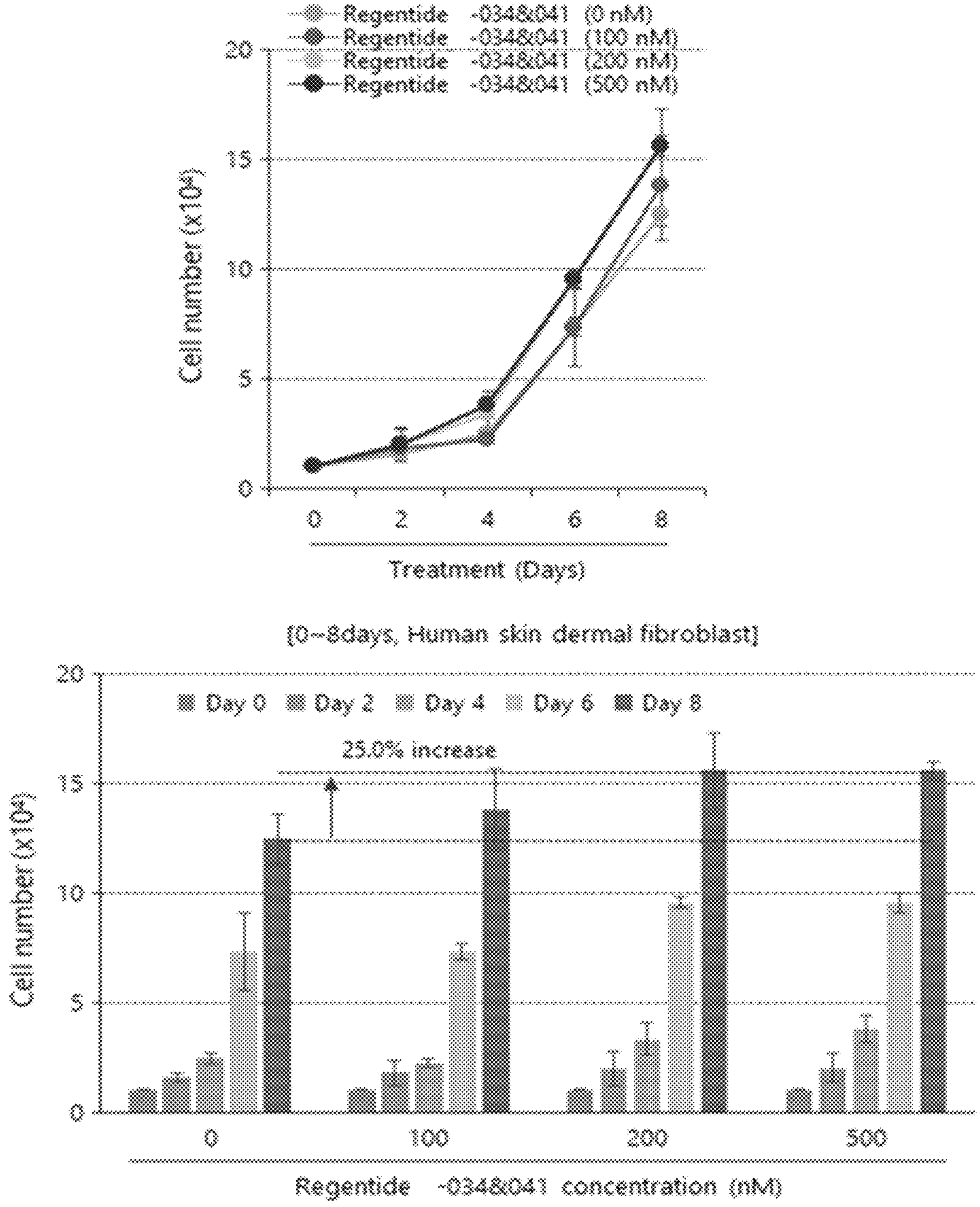
FIG. 6 is a view showing the results of confirming the fibroblast growth promoting efficacy of the mixture of Regentide-034 and Regentide-041 according to the present invention.

As shown in FIG. 6, it was confirmed that the group treated with the mixture of Regentide-034 and Regentide-041 promoted the growth of fibroblasts in a concentration and time-dependent manner. In particular, after 8 days of treatment with the mixture of Regentide-034 and Regentide-041, it was confirmed that the cell growth rate of the group treated with the mixture at 500 nM was about 25% higher than that of the control group.

Example 6. Confirmation of Wound Healing Effect of a Mixture of Regentide-034 and Regentide-041

6-1. Confirmation of Wound Healing Effect on Epidermal Keratinocytes

In order to confirm the wound healing effect of a mixture of Regentide-034 and Regentide-041, adhesive inserts (Insert, Ibidi, Wisconsin, USA) were attached to a 6-well plate, and HaCaT cells, which are epidermal keratinocytes were seeded in each well of the insert at $6\times10^4$ cells/well. They were cultured in cell culture conditions for 24 hours in a medium containing 2% FBS. The insert was then removed, and they were washed once with 1×DPBS. Mixtures of Regentide-034 and Regentide- 041 were added to the medium without FBS at various concentrations (0, 1, or 2.5 μM). After 16 and 40 hours, cells were imaged at 100× using a microscope (Nikon™ microscpe Eclipse E100, Tokyo, Japan). The micrographs taken are shown in FIG. 7.

Figure 7:
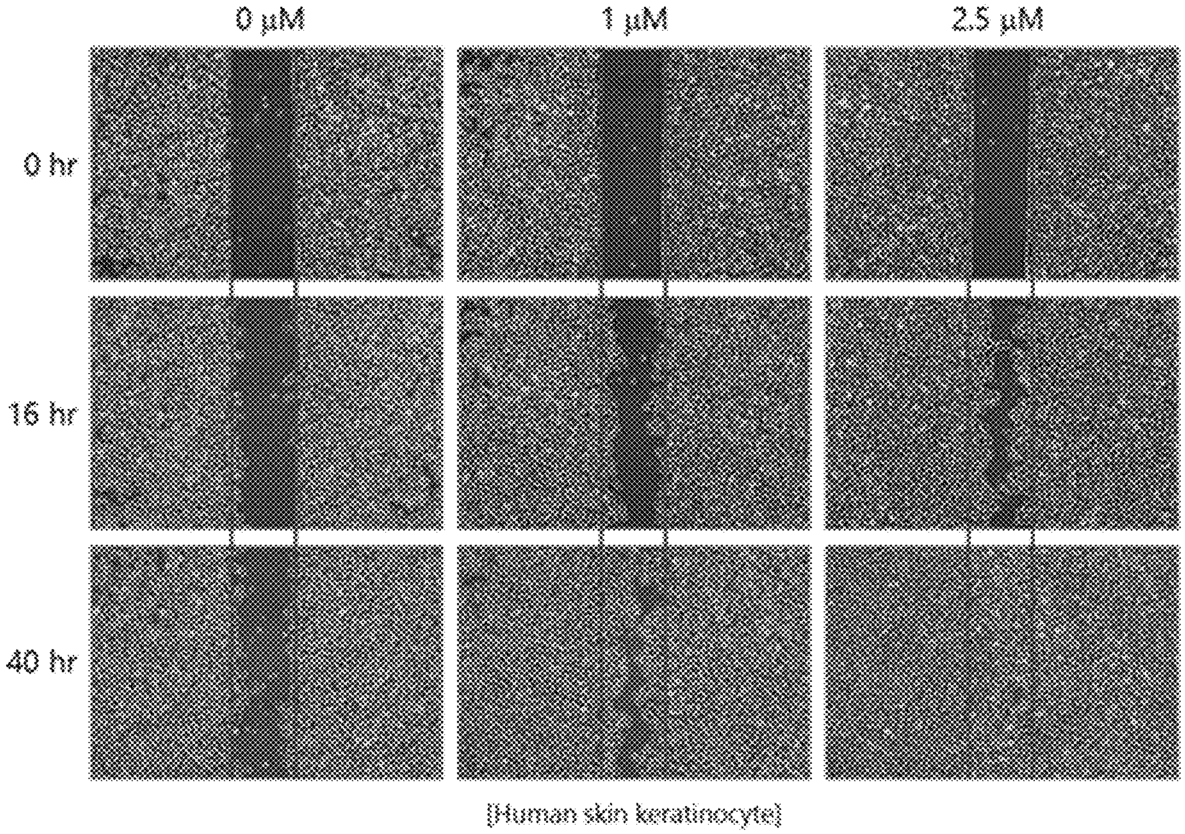
FIG. 7 is a view showing the results of confirming the wound healing effect on the epidermal keratinocytes of the mixture of Regentide-034 and Regentide-041 according to the present invention.

As shown in FIG. 7, it was confirmed that all of the groups treated with a mixture of Regentide-034 and Regentide-041 increased the cell number and cell migration ability of epidermal keratinocytes.

6-2. Wound Healing Effect on Fibroblasts

In order to confirm the wound healing effect of a mixture of Regentide-034 and Regentide-041, adhesive inserts (Insert, Ibidi, Wisconsin, USA) were attached to a 6-well plate, and CCD-986sk, which are dermal cells, were seeded in each well of the insert at $6\times10^4$ cells/well. They were cultured in cell culture conditions for 24 hours in a medium containing 2% FBS. The insert was then removed, and they were washed once with 1×DPBS. Mixtures of Regentide-034 and Regentide-041 were added to the medium without FBS at various concentrations (0, 1, or 2.5 μM). After 16 and 40 hours, cells were imaged at 100× using a microscope (Nikon™ microscope Eclipse E100, Tokyo, Japan). The micrographs taken are shown in FIG. 8.

Figure 8:
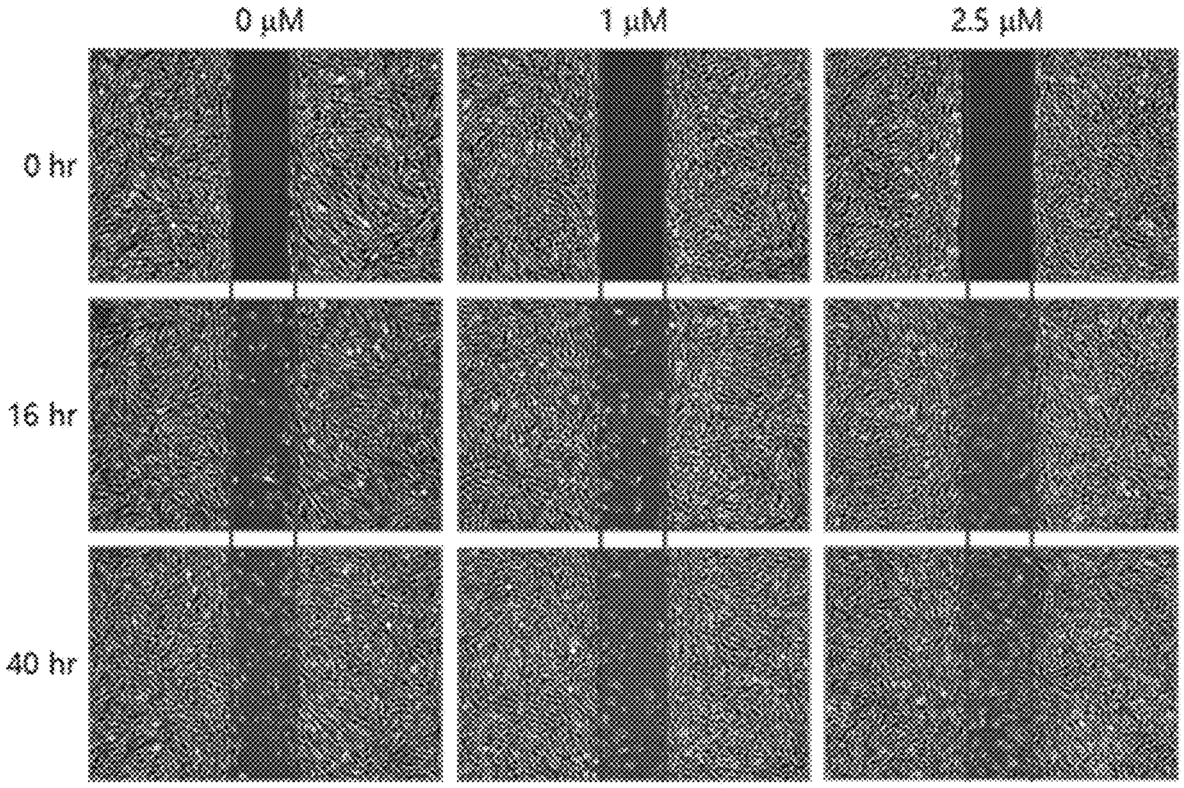
FIG. 8 is a diagram showing the results of confirming the wound healing effect on fibroblasts of the mixture of Regentide-034 and Regentide-041 according to the present invention.

As shown in FIG. 8, it was confirmed that all of the groups treated with a mixture of Regentide-034 and Regentide-041 increased the cell number and cell migration ability of fibroblasts.

From the above results, it was confirmed that the mixture of Regentide-034 and Regentide-041 increased the skin cell number and increased cell migration ability, which means that it may induce faster recovery of wounds such as cuts.

Figure 9:
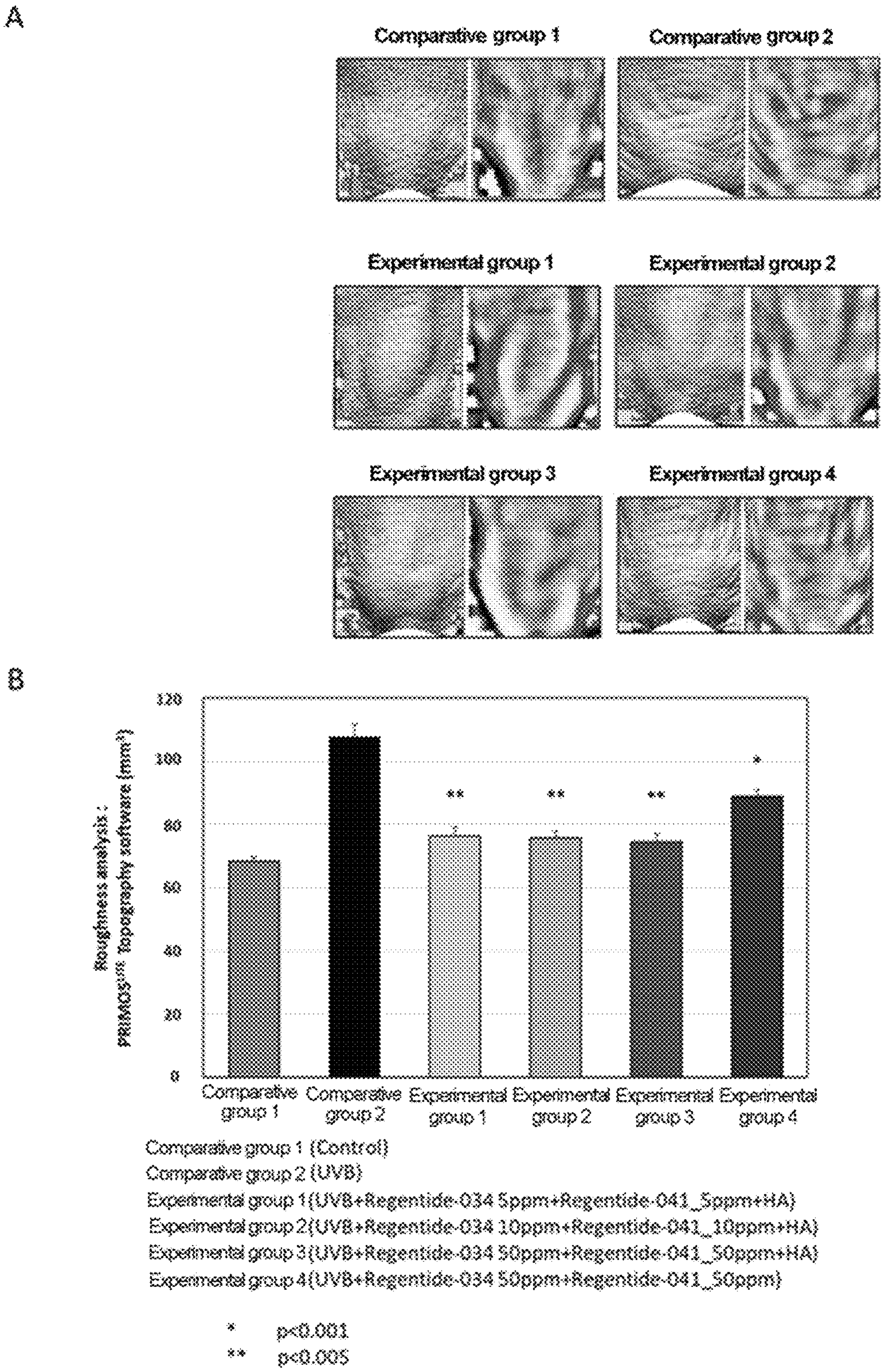
FIG. 9 is a view showing the results of confirming the improvement effect on wrinkle due to photoaging of a mixture of Regentide-034 and Regentide-041 according to the present invention in an animal model.

Example 7. Confirmation of Improvement Effect of a Mixture of Regentide-034 and Regentide-041 on Wrinkle by Photoaging in Animal Model To measure the improvement effect of a mixture of Regentide-034 and Regentide-041 on wrinkle by photoaging, 6-week-old female hairless mice (SKH, HR-1) were purchased from Orient Bio for use. All mice were bred at a 12 hr/day light/dark cycle in a laboratory maintained at optimum environmental conditions with a temperature of 24±2° C. and a humidity of 50±10%, and food was allowed to be freely eaten. Before the experiment, a stabilization period of at least 1 week was allowed, and the experiment was started after acclimatization. This evaluation was carried out after approval (No. 202000058) of the Institutional Animal Care and Use Committee operated by Chung-Ang University College of Medicine. As shown in FIG. 9, in order to induce shallow wrinkles due to photoaging on the back of experimental animals for photoaging model production, UVB was irradiated for 24 weeks, 2 to 3 times a week using BIO-SPECTRA (Virber Rourmat, France). After the experimental animals were anesthetized (Zoletil:Rompun=3:1), a group on which a total of 10 ppm, 20 ppm, or 100 ppm of a mixture of Regentide-034 and Regentide-041 and hyaluronic acid (HA) were mixed in a ratio of 1:1 and a group in which 100 ppm of the mixture of Regentide-034 and Regentide-041 was used in a ratio of 1:1 without hyaluronic acid were injected into the mouse back area. In all experimental groups, 200 µl was injected subcutaneously into the wrinkles linearly. The degree of wrinkle improvement in the administered group was evaluated according to the lapse of 0 hours, 1 week, 2 weeks, and 4 weeks after injection. Thirteen mice were used per group, and five mice were used for persistence evaluation and eight mice were used for tissue staining. The amount of wrinkle change was analyzed using PRIMOSLITE (GFMesstechnikGmbH, Germany). Software PRIMOS 5.8 was used for the analysis program, and the roughness (Roughness parameter, Rmax) that may confirm the wrinkle change was utilized through this evaluation. After wrinkle induction, a group was treated with the mixture of Regentide-034 and Regentide-041 and hyaluronic acid, and a group was treated without hyaluronic acid. After the progress of 4 weeks period, the roughness for the wrinkle change was measured. The results of confirming the improvement effect on wrinkle due to photoaging are shown in FIGS. 9A and 9B.

As shown in FIG. 9A, it was confirmed that the group irradiated with ultraviolet rays in Comparative Group 2 (UVB) produced many skin wrinkles compared to Comparative Group 1 (Control). Meanwhile, it was confirmed that the generation of wrinkles in Experimental Group 1 (Regentide-034_5 ppm+Regentide-041_5 ppm+HA), Test Group 2 (Regentide-034_10 ppm+Regentide-041_10 ppm+HA), Experimental Group 3 (Regentide-034_50 ppm+Regentide-041_50 ppm+HA), and Experimental Group 4 (Regentide-034_50 ppm+Regentide-041_50 ppm) was less than that of the UV-irradiated group of Comparative Group 2 (UVB).

As shown in FIG. 9B, the result of confirming the roughness (Roughness parameter, R max) that may confirm the wrinkle change through PRIMOSLITE (GFMesstechnikGmbH, Germany) indicated that the generation of wrinkles was increased by about 50% in the UV-irradiated group of Comparative Group 2 (UVB) compared to Comparative Group 1 (Control). It was confirmed that Experimental group 1 (UVB+Regentide-034_5 ppm+Regentide-041_5 ppm+HA), Experimental group 2 (UVB+Regentide-034_10 ppm+Regentide-041_10 ppm+HA) and Experimental group 3 (UVB+Regentide-034_50 ppm+Regentide-041_50 ppm+HA), respectively, had the wrinkle improvement effect by about 29%, 30% and 31% compared to the only UV-irradiated group of Comparative Group 2 (UVB), confirming about 30% of the wrinkle improvement effect in Experimental groups containing the mixture of Regentide-034 and Regentide-041 and hyaluronic acid, and it was confirmed that there was statistical significance (**, $p<0.001$). In addition, it was confirmed that in the case of the Experimental group treated only with Regentide-034 and Regentide-041, which is Experimental Group 4 (UVB+Regentide-034_50 ppm+Regentide-041_50 ppm) excluding hyaluronic acid, the wrinkle improvement effect was increased by 17% compared to the UV-irradiated group of Comparative Group 2 (UVB), and it was confirmed that there was statistical significance (*, $p<0.001$). These results confirmed that the mixture of Regentide-034 and Regentide-041 had the effect of improving skin wrinkles induced by UV rays.

The above results confirm that the UV-induced skin wrinkle improvement ability is enhanced by using a mixture of hyaluronic acid and Regentide-034 and Regentide-041 used in the filler, which may be used as a filler material.

Example 8. Confirmation of Collagen Expression Level and Elastin Expression Level by a Mixture of Regentide-034 and Regentide-041 in Wrinkled Animal Model In order to confirm the collagen expression level and the elastin expression level by the mixture of Regentide-034 and Regentide-041 in the wrinkled animal model caused by photoaging, a total of six experimental animals of Comparative Group 1, Comparative Group 2, and Experimental Groups 1 to 4 of Example 7 were sacrificed, and the skin tissue injected with the test group was extracted and fixed in 10% neutral buffered formalin solution. Thereafter, they were embedded in paraffin, hardened, and 5 µm sections were prepared. The amount of collagen production was confirmed by Masson's trichrome (MT) stain and the amount of elastin production was confirmed by Verhoeff-Van Gieson (VVG) stain. After observing the tissue slides at 200 magnification using a tissue slide scanner (Leica™, Aperio™ CS2Slide Scanner, USA), the major histological characteristics for each slide were read to evaluate the expression levels of collagen and elastin production in tissues. The results of confirming the expression levels of collagen and elastin production, respectively, are shown in FIGS. 10A and 10B.

Figure 10:
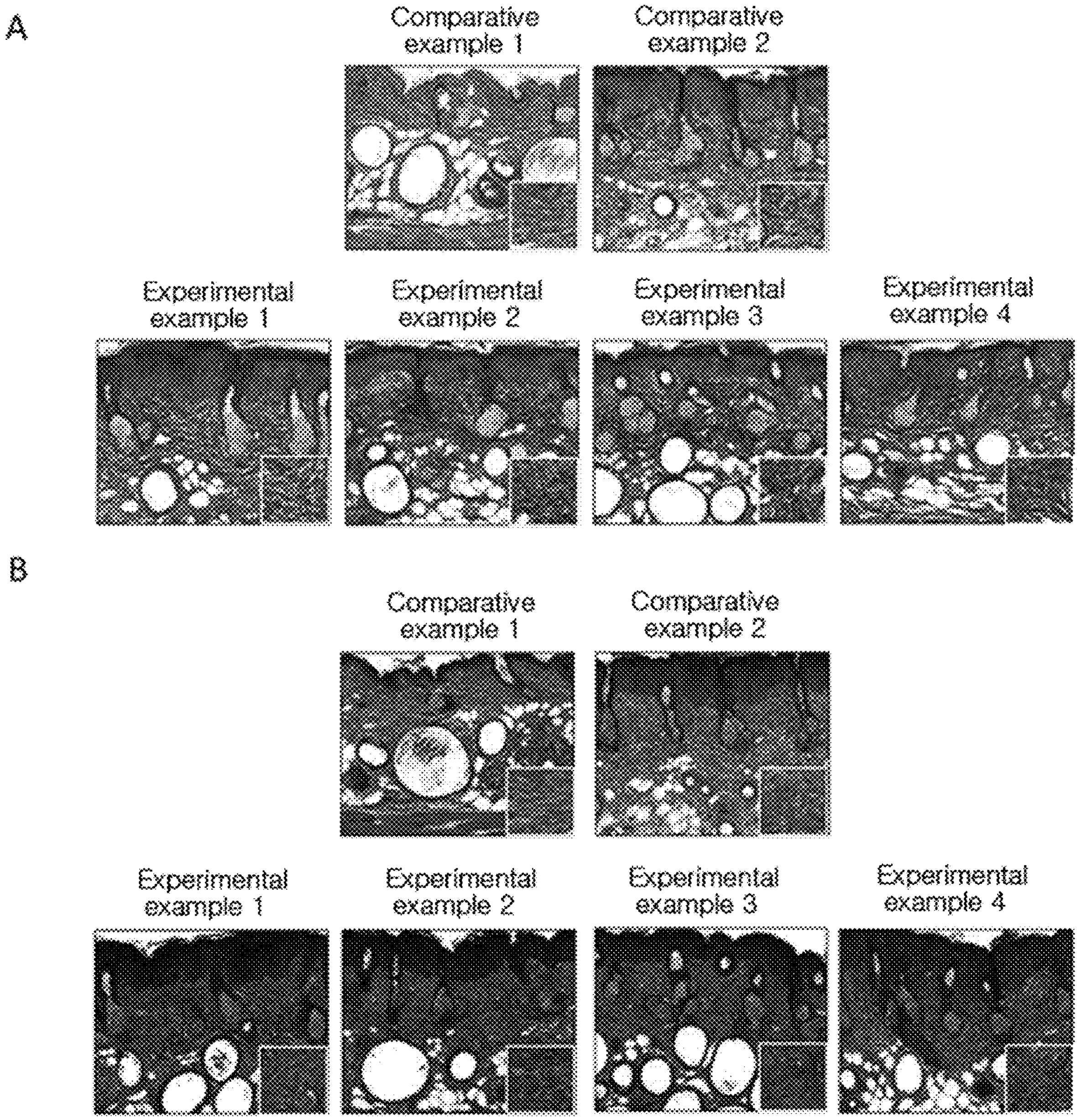
FIG. 10 is a view showing the results of confirming the collagen and elastin expression levels of a mixture of Regentide-034 and Regentide-041 according to the present invention in an animal model.

As shown in FIG. 10A, the results of comparing the collagen expression level, it was confirmed that the collagen expression level was increased in Experimental group 1 (Regentide-034_5 ppm+Regentide-041_5 ppm+HA), Experimental group 2 (Regentide-034_10 ppm+Regentide- 041_10 ppm+HA), Experimental group 3 (Regentide-034_50 ppm+Regentide-041_50 ppm+HA), and Experimental group 4 (Regentide-034_50 ppm+Regentide-041_50 ppm) compared to Comparative group 1 (Control) and Comparative group 2 (UVB).

As shown in FIG. 10B, the results of comparing the elastin expression level, it was confirmed that the elastin expression level was increased in Experimental group 1 (Regentide-034_5 ppm+Regentide-041_5 ppm+HA), Experimental group 2 (Regentide-034_10 ppm+Regentide-041_10 ppm+HA), Experimental group 3 (Regentide-034_50 ppm+Regentide-041_50 ppm+HA), and Experimental group 4 (Regentide-034_50 ppm+Regentide-041_50 ppm) compared to Comparative group 1 (Control) and Comparative group 2 (UVB).

The above result means that the mixture of Regentide-034 and Regentide-041 has the effect of improving the skin wrinkles induced by UV rays by increasing the collagen and elastin expression levels in the skin.

Hereinafter, the present invention is described in more detail through formulation examples. The formulation examples are only for illustrating the present invention, and the scope of the present invention is not to be construed as being limited by the formulation examples.

Formulation Example 1. Preparation of a Cosmetic Formulation

1-1. Preparation of Softening Lotion

A softening lotion was prepared by mixing 0.1% by weight of a mixture of Regentide-034 and Regentide-041, 5.2% by weight of 1,3-butylene glycol, 1.5% by weight of oleyl alcohol, 3.2% by weight of ethanol, 3.2% by weight of polysorbate 20, 2.0% by weight of benzophenone-9, 1.0% by weight of carboxyl vinyl polymer, 3.5% by weight of glycerin, a trace amount of fragrance, a trace amount of a preservative and the remaining amount of purified water in a conventional method.

1-2. Preparation of Milk Lotion

A milk lotion was prepared by mixing 0.1% by weight of a mixture of Regentide-034 and Regentide-041, 5.1% by weight of glycerin, 4.2% by weight of propylene glycol, 3.0% by weight of tocopheryl acetate, 4.6% by weight of liquid paraffin, 1.0% by weight of triethanolamine, 3.1% by weight of squalane, 2.5% by weight of macadamia nut oil, 1.6% by weight of polysorbate 60, 1.6% by weight of sorbitan sesquioleate, 0.6% by weight of propylparaben, 1.5% by weight of carboxyl vinyl polymer, a trace amount of fragrance, a trace amount of preservative, and the remaining amount of purified water in a conventional method.

1-3. Preparation of Nourishing Cream

A nourishing cream was prepared by mixing 0.5% by weight of a mixture of Regentide-034 and Regentide-041, 4.0% by weight of glycerin, 3.5% by weight of petrolatum, 2.1% by weight of triethanolamine, 5.3% by weight of liquid paraffin, 3.0% by weight of squalane, 2.6% by weight of beeswax, 5.4% by weight of tocopheryl acetate, 3.2% by weight of polysorbate 60, 1.0% by weight of carboxyl vinyl polymer, 3.1% by weight of sorbitan sesquioleate, a trace amount of fragrance, a trace amount of preservative, and the remaining amount of purified water in a conventional method.

1-4. Preparation of Massage Cream

A massage cream was prepared by mixing 0.5% by weight of a mixture of Regentide-034 and Regentide-041, 4.0% by weight of glycerin, 3.5% by weight of petrolatum, 0.5% by weight of triethanolamine, 24.0% by weight of liquid paraffin, 3.0% by weight of squalane, 2.1% by weight of beeswax, 0.1% by weight of tocopheryl acetate, 2.4% by weight of polysorbate 60, 1.0% by weight of carboxyl vinyl polymer, 2.3% by weight of sorbitan sesquioleate, a trace amount of fragrance, a trace amount of preservative, and the remaining amount of purified water in a conventional method.

1-5. Preparation of Body Cleanser for Cleaning

A body cleanser for cleaning was prepared by mixing 1 g of a mixture of Regentide-034 and Regentide-041, 18 g of anionic surfactant, 5 g of nonionic surfactant, 7 g of glycerin, 3 g of sodium chloride, 1.5 g of natural olive liquid soap, 1 g of fragrance, and 100 g of water in a conventional manner.

Hereinabove, specific parts of the present invention have been described in detail. It is clear for those of ordinary skill in the art that these specific descriptions are only preferred embodiments, and the scope of the present invention is not limited thereby. Accordingly, it is intended that the substantial scope of the present invention be defined by the appended claims and their equivalents.

The invention claimed is:

1. A method for skin condition improvement, the method comprising a step of administering a composition comprising a peptide consisting of the amino acid sequence of SEQ ID NO: 1 with an amine group,-$NH_2$, conjugated to the C-terminal thereof, and a peptide consisting of the amino acid sequence of SEQ ID NO: 2 with an amine group,—$NH_2$, conjugated to the C-terminal thereof" in place of the current recitation of "a peptide consisting of the amino acid sequence of SEQ ID NO: 1 and a peptide consisting of the amino acid sequence of SEQ ID NO: 2, wherein said peptides include an amine group (—$NH_2$) conjugated to the C-terminal thereof, wherein said peptides are mixed in a concentration ratio of 1:1 to 1:10 and administered simultaneously, and wherein the skin condition improvement includes at least one selected from the group consisting of skin aging improvement, skin regeneration, skin elasticity improvement, skin wrinkle prevention, skin wrinkle improvement and skin wound regeneration.

2. The method of claim 1, wherein the composition is a cosmetic composition, quasi-drug composition, food composition, health functional food composition or filler composition.

3. The method of claim 1, wherein the skin aging includes photoaging or natural aging.

4. The method of claim 1, wherein the peptide consisting of the amino acid sequence of SEQ ID NO: 1 or 2 has a concentration of 0.1 μM to 1,000 μM.

5. The method of claim 1, wherein the composition is formulated in a filler.

6. A filler for skin injection, the filler comprising: a peptide consisting of the amino acid sequence of SEQ ID NO: 1 with an amine group,-$NH_2$, conjugated to the C-terminal thereof, and a peptide consisting of the amino acid sequence of SEQ ID NO: 2 with an amine group,—$NH_2$, conjugated to the C-terminal thereof" in place of the current recitation of "a peptide consisting of the amino acid sequence of SEQ ID NO: 1 and a peptide consisting of the amino acid sequence of SEQ ID NO: 2, wherein said peptides include an amine group (—$NH_2$) conjugated to the C-terminal thereof, and wherein said peptides are mixed in a concentration ratio of 1:1 to 1:10 and administered simultaneously.

7. The filler of claim 6, wherein the filler is for skin condition improvement, and wherein the skin condition improvement includes at least one selected from the group consisting of skin aging improvement, skin regeneration, skin elasticity improvement, skin wrinkle prevention, skin wrinkle improvement and skin wound regeneration.

8. A method for treating a wound, the method comprising a step of administrating to an individual in need thereof a peptide consisting of the amino acid sequence of SEQ ID NO: 1 with an amine group,-$NH_2$, conjugated to the C-terminal thereof, and a peptide consisting of the amino acid sequence of SEQ ID NO: 2 with an amine group,—$NH_2$, conjugated to the C-terminal thereof" in place of the current recitation of "a peptide consisting of the amino acid sequence of SEQ ID NO: 1 and a peptide consisting of the amino acid sequence of SEQ ID NO: 2, wherein said peptides include an amine group (—$NH_2$) conjugated to the C-terminal thereof, and wherein said peptides are mixed in a concentration ratio of 1:1 to 1:10 and administered simultaneously.

* * * * *

SEQUENCE LISTING

```
<160> NUMBER OF SEQ ID NOS: 4

<210> SEQ ID NO 1
<211> LENGTH: 10
<212> TYPE: PRT
<213> ORGANISM: Artificial
<220> FEATURE:
<223> OTHER INFORMATION: Peptide-034

<400> SEQUENCE: 1

Ala Tyr Gly Cys Tyr Cys Gly Trp Gly Gly
1               5                   10


<210> SEQ ID NO 2
<211> LENGTH: 12
<212> TYPE: PRT
<213> ORGANISM: Artificial
<220> FEATURE:
<223> OTHER INFORMATION: Peptide-041
```

-continued

```
<400> SEQUENCE: 2

Cys Ile Pro Arg Gly Gly Ile Cys Leu Val Ala Leu
1               5                   10


<210> SEQ ID NO 3
<211> LENGTH: 10
<212> TYPE: PRT
<213> ORGANISM: Artificial
<220> FEATURE:
<223> OTHER INFORMATION: Regentide-034
<220> FEATURE:
<221> NAME/KEY: NON_TER
<222> LOCATION: (10)..(10)
<223> OTHER INFORMATION: amine group

<400> SEQUENCE: 3

Ala Tyr Gly Cys Tyr Cys Gly Trp Gly Gly
1               5                   10


<210> SEQ ID NO 4
<211> LENGTH: 12
<212> TYPE: PRT
<213> ORGANISM: Artificial
<220> FEATURE:
<223> OTHER INFORMATION: Regentide-041
<220> FEATURE:
<221> NAME/KEY: NON_TER
<222> LOCATION: (12)..(12)
<223> OTHER INFORMATION: amine group

<400> SEQUENCE: 4

Cys Ile Pro Arg Gly Gly Ile Cys Leu Val Ala Leu
1               5                   10
```